(12) United States Patent
Oka et al.

(10) Patent No.: US 8,216,597 B2
(45) Date of Patent: Jul. 10, 2012

(54) OIL-IN-WATER EMULSION COMPOSITION AND METHOD FOR PRODUCING THE SAME

(75) Inventors: Takashi Oka, Yokohama (JP); Reiji Miyahara, Yokohama (JP); Takashi Teshigawara, Yokohama (JP)

(73) Assignee: Shiseido Company Ltd., Chuo-ku, Tokyo (JP)

(*) Notice: Subject to any disclaimer, the term of this patent is extended or adjusted under 35 U.S.C. 154(b) by 247 days.

(21) Appl. No.: 12/670,895

(22) PCT Filed: Jul. 22, 2008

(86) PCT No.: PCT/JP2008/063106
§ 371 (c)(1),
(2), (4) Date: Jan. 27, 2010

(87) PCT Pub. No.: WO2009/016989
PCT Pub. Date: Feb. 5, 2009

(65) Prior Publication Data
US 2010/0196429 A1    Aug. 5, 2010

(30) Foreign Application Priority Data

Jul. 27, 2007 (JP) ................................ 2007-195719
Feb. 29, 2008 (JP) ................................ 2008-049393

(51) Int. Cl.
| A61K 8/02 | (2006.01) |
| A61K 8/00 | (2006.01) |
| A61K 9/14 | (2006.01) |
| A61K 9/66 | (2006.01) |
| A61Q 19/02 | (2006.01) |

(52) U.S. Cl. .......... 424/401; 424/63; 424/489; 424/455; 424/62

(58) Field of Classification Search .............. 424/62, 424/63, 401, 455, 489
See application file for complete search history.

(56) References Cited

U.S. PATENT DOCUMENTS

| 5,391,321 | A | * | 2/1995 | Gruning et al. ............... 516/22 |
| 7,534,369 | B2 | * | 5/2009 | Suzuki et al. ............ 252/299.01 |
| 2002/0106387 | A1 | * | 8/2002 | Nishida et al. ................ 424/401 |
| 2007/0253925 | A1 | * | 11/2007 | Arkles et al. ............... 424/70.12 |

FOREIGN PATENT DOCUMENTS

| JP | 4-243806 | 8/1992 |
| JP | 2002-29915 | 1/2002 |

(Continued)

OTHER PUBLICATIONS

International Search Report for corresponding PCT/JP2008/063106 mailed Oct. 28, 2008, three pages.

*Primary Examiner* — Aradhana Sasan
(74) *Attorney, Agent, or Firm* — Rankin, Hill & Clark LLP (57) ABSTRACT

The present invention provides: an oil-in-water emulsion composition, into which an oil-soluble drug is stably incorporated and which is excellent in feeling during use; and a method for producing the aforementioned composition, which does not require complicated operations. An oil-in-water emulsion composition comprising; (A) a polyoxyethylene phytosterol, (B) a glycerin fatty acid diester, (C) a polyoxyethylene-polyoxypropylene random copolymer dialkyl ether, (D) an oil-soluble drug, (E) oil, and (F) water; wherein a layered gel structure composed of the components (A) and (B) is present in an emulsion particle in the emulsion composition.

21 Claims, 4 Drawing Sheets

FOREIGN PATENT DOCUMENTS

| | | |
|---|---|---|
| JP | 2006-111620 | 4/2006 |
| JP | 2007-14866 * | 1/2007 |
| JP | 2007-153801 | 6/2007 |
| JP | 2007-254405 | 10/2007 |
| JP | 2007-332037 | 12/2007 |
| JP | 2008-137966 | 6/2008 |

* cited by examiner

Test Example 1-1
(oil-in-water emulsion composition)

added to an
aqueous formulation

Test Example 3-1
(lotion)

FIG.8

OIL-IN-WATER EMULSION COMPOSITION AND METHOD FOR PRODUCING THE SAME

RELATED APPLICATIONS

This application claims the priority of Japanese Patent Application No. 2007-195719 filed on Jul. 27, 2007 and Japanese Patent Application No. 2008-049393 filed on Feb. 29, 2008, which are incorporated herein by reference.

FIELD OF THE INVENTION

The present invention relates to an oil-in-water emulsion composition and a method for producing the same, and particularly to the improvement of the stability and feeling during use of an oil-in-water emulsion composition, into which an oil-soluble drug is incorporated, and the simplification of a method for producing such oil-in-water emulsion composition.

BACKGROUND OF THE INVENTION

Conventionally, the development of a pharmaceutical agent has been vigorously carried out for incorporating an oil-soluble drug as an active ingredient into a base material. In particular, since the fact that corneocyte lipids existing on the surface of the skin, such as ceramide, are deeply associated with the barrier function of the stratum corneum has been revealed, the development of a pharmaceutical agent, into which such corneocyte lipids are mixed, has been attempted. However, such ceramides have high crystallinity, and thus, when they have been incorporated into a cosmetic product, the incorporated amounts have been limited from the viewpoint of stability. As a result, the effect of incorporating such ceramides has not been sufficiently obtained. Hence, it has been desired to develop a cosmetic product, which maintains high stability and which does not cause problems regarding the precipitation of crystals and the like even if ceramides are incorporated therein in amounts allowing the effect of the ceramides to be sufficiently expressed.

In order to achieve the object, there have been studied, for example, a method for finely and stably incorporating a lipid by using a nonionic surfactant and an ionic surfactant in combination (see Patent Document 1, for example), a method for forming liquid crystal using a lipid, a surfactant, and an oil (see Patent Document 2, for example), a method using a complex obtained by precipitating a lipid and a surfactant from an organic solvent (see Patent Document 3, for example), a method using a liposome (a vesicle consisting of a phospholipid bimolecular membrane), and the like.

However, in general, ceramides such as sphinganine have poor solubility in an oil. Accordingly, even in the aforementioned methods, relatively large amounts of surfactants and solvents need to be incorporated, and thus the produced cosmetic products have been problematic in terms of safety. In particular, when such ceramides are incorporated into a cosmetic product, which hates the incorporating of an organic solvent, a technique of completely removing a large amount of organic solvent used to obtain a complex consisting of a lipid and a surfactant has been necessary, and complicated operations should have been conducted in the production process of the cosmetic product. Moreover, as for the method using a liposome, since a phospholipid is generally an unstable substance, it has been difficult to sufficiently ensure high-temperature stability and long-term stability, when the liposome has been incorporated into a cosmetic product.

Patent literature 1: Japanese Unexamined Patent Publication H4-193814
Patent literature 2: Japanese Unexamined Patent Publication H6-345633
Patent literature 3: Japanese Unexamined Patent Publication H11-199462

DISCLOSURE OF THE INVENTION

Problem to be Solved by the Invention

The present invention has been made to solve the aforementioned problems of the prior art techniques. Thus, it is an object of the present invention to provide: an oil-in-water emulsion composition, into which an oil-soluble drug is stably incorporated and which is excellent in feeling during use; and a method for producing the composition, which does not require complicated operations.

Means to Solve the Problem

As a result of intensive studies directed towards achieving the aforementioned object, the present inventors have found that fine emulsion particles each containing a layered gel structure therein and being in the form of capsule composed of an internal phase oil coated with the layered gel structure can be formed by preparing an oil-in-water emulsion composition comprising an oil-soluble drug, using a polyoxyethylene phytosterol, a glycerin fatty acid diester, and a polyoxyethylene-polyoxypropylene random copolymer dialkyl ether. As a result, an oil-in-water emulsion composition in which oil containing the oil-soluble drug is extremely stably maintained in the internal oil phase and which is excellent in terms of feeling during use, can be easily produced. Thereby the present inventors have accomplished the present invention.

Specifically, the oil-in-water emulsion composition according to the present invention comprises; (A) a polyoxyethylene phytosterol, (B) a glycerin fatty acid diester, (C) a polyoxyethylene-polyoxypropylene random copolymer dialkyl ether, (D) an oil-soluble drug, (E) oil, and (F) water; wherein a layered gel structure composed of the components (A) and (B) is present in an emulsion particle in the emulsion composition.

Moreover, in the oil-in-water emulsion composition, it is preferably that a part or the entire emulsion particles are in the form of capsule composed of an internal phase oil coated with the layered gel structure.

Moreover, the oil-in-water emulsion composition preferably comprises a polyoxyethylene-polyoxypropylene random copolymer dimethyl ether as the (C) polyoxyethylene-polyoxypropylene random copolymer dialkyl ether.

Moreover, in the oil-in-water emulsion composition, the (D) oil-soluble drug is preferably one or more selected from the group consisting of an emollient agent, a skin-whitening agent, a skin roughness-preventing agent, an ultraviolet absorber, an anti-inflammatory agent, vitamins, and an antioxidant.

Moreover, the oil-in-water emulsion composition preferably comprises a higher fatty acid containing 8 to 20 carbon atoms and/or a higher alcohol containing 8 to 20 carbon atoms as the (E) oil.

Moreover, the oil-in-water emulsion composition preferably comprises isostearic acid as the higher fatty acid.

Moreover, the oil-in-water emulsion composition preferably comprises isostearyl alcohol as the higher alcohol.

Moreover, in the oil-in-water emulsion composition, emulsion particles with the internal oil phase each preferably have a diameter of 50 to 1,000 nm.

Moreover, a method for producing the oil-in-water emulsion composition according to the present invention comprises; a step of mixing (A) a polyoxyethylene phytosterol, (B) a glycerin fatty acid diester, (C) a polyoxyethylene-polyoxypropylene random copolymer dialkyl ether, (D) an oil-soluble drug, and (E) oil to form an oil component mixture containing a layered gel structure composed of the components (A) and (B); and a step of adding an aqueous component containing (F) water into the oil component mixture obtained in the above step and mixing them to form an oil-in-water emulsion.

Moreover, the oil-in-water emulsion cosmetic product according to the present invention comprises the above oil-in-water emulsion composition.

Effect of the Invention

According to the present invention, by preparing an oil-in-water emulsion composition using polyoxyethylene phytosterol, glycerin fatty acid diester, and polyoxyethylene-polyoxypropylene random copolymer dialkyl ether, a layered gel structure can be formed in an emulsion particle and an internal phase oil is coated with the layered gel structure to form a capsule. As a result, an oil-in-water emulsion composition, in which an oil-soluble drug is extremely stably maintained in the internal oil phase and which is excellent in terms of feeling during use, can be easily produced.

BRIEF DESCRIPTION OF THE DRAWINGS

FIG. 7 shows photographs of a transmission electron microscope (TEM) of the oil-in-water emulsion composition (Test Example 1-1) and the cosmetic product (Test Example 3-1) according to the present invention.

BEST MODE FOR CARRYING OUT THE INVENTION

The oil-in-water emulsion composition according to the present invention comprises; (A) a polyoxyethylene phytosterol, (B) a glycerin fatty acid diester, (C) a polyoxyethylene-polyoxypropylene random copolymer dialkyl ether, (D) an oil-soluble drug, (E) oil, and (F) water; wherein a layered gel structure composed of the components (A) and (B) is present in an emulsion particle in the emulsion composition.

It is to be noted that the term the "oil-in-water emulsion composition" according to the present invention is used herein to mean both an oil-in-water emulsion composition (1) consisted of the components (A) to (F), and an oil-in-water emulsion composition (2) obtained by further adding the oil-in-water emulsion composition (1) as a base material into an aqueous component.

(A) Polyoxyethylene Phytosterol

The (A) polyoxyethylene phytosterol used in the oil-in-water emulsion composition of the present invention is not particularly limited. For instance, polyoxyethylene phytosterols having 5 to 50 moles of oxyethylene can be preferably used. Specific examples of such polyoxyethylene phytosterol include polyoxyethylene (5 moles) phytosterol, polyoxyethylene (10 moles) phytosterol, polyoxyethylene (20 moles) phytosterol, and polyoxyethylene (30 moles) phytosterol. Commercially available products of such polyoxyethylene phytosterol include NIKKOL BPS-5, NIKKOL BPS-10, NIKKOL BPS-20, and NIKKOL BPS-30 (all manufactured by Nihon Surfactant Kogyo K.K.).

The incorporated amount of (A) polyoxyethylene phytosterol is not particularly limited. The polyoxyethylene phytosterol is incorporated at a mass percentage of preferably 1% to 15%, and more preferably 3% to 10%, with respect to the total mass of the oil-in-water emulsion composition (1) of the present invention. If the incorporated amount is less than 1% by mass, stable and uniform emulsion particles may not be obtained. On the other hand, if the incorporated amount exceeds 15% by mass, the amount of a surfactant becomes too large when the composition is used for a cosmetic product or the like, and thus it is unfavorable in terms of safety.

(B) Glycerin Fatty Acid Diester

The type of (B) glycerin fatty acid diester used in the oil-in-water emulsion composition of the present invention is not particularly limited, as long as it is a compound in which two hydroxyl groups of glycerin (which are generally two hydroxyl groups at both ends) bind to a fatty acid via an ester bond. For instance, a compound in which such two hydroxyl groups of glycerin bind to a linear or branched higher fatty acid containing 8 to 20 carbon atoms via an ester bond can be preferably used. Specific examples of such glycerin fatty acid diester include glyceryl di-2-heptylundecanoate and glyceryl pyroglutamate oleate. Commercially available products of such glycerin fatty acid diester include SUN ESPOL G-218 (manufactured by Taiyo Kagaku Co., Ltd.), Ami Gly P-30V (manufactured by Taiyo Kagaku Co., Ltd.), and Ami Gly P-30 (manufactured by Taiyo Kagaku Co., Ltd.). A particularly preferred glycerin fatty acid diester is glyceryl di-2-heptylundecanoate.

The incorporated amount of (B) glycerin fatty acid diester is not particularly limited. The glycerin fatty acid diester is incorporated at a mass percentage of preferably 1% to 10%, and more preferably 2% to 8%, with respect to the total mass of the oil-in-water emulsion composition (1) of the present invention. If the incorporated amount is less than 1% by mass, an oil-soluble drug may not be stably maintained. On the other hand, if the incorporated amount exceeds 10% by mass, there may be a case in which feeling during use becomes poor, for example, stickiness is generated, when the composition is used for a cosmetic product or the like.

(C) Polyoxyethylene-polyoxypropylene Random Copolymer Dialkyl Ether

The type of (C) polyoxyethylene-polyoxypropylene random copolymer dialkyl ether used in the oil-in-water emulsion composition of the present invention is not particularly limited, as long as it is a compound generally used for cosmetic products. Examples of such polyoxyethylene-polyoxypropylene random copolymer dialkyl ether include polyoxyethylene-polyoxypropylene copolymer dimethyl ether and polyoxyethylene-polyoxypropylene copolymer diethyl ether. The additive forms of a polyoxyethylene group and a polyoxyalkylene group in the copolymer need to be random types. A particularly preferred polyoxyethylene-polyoxypropylene random copolymer dialkyl ether is a polyoxyethylene (14 moles) polyoxypropylene (7 moles) dimethylether random copolymer.

(C) Polyoxyethylene-polyoxypropylene random copolymer dialkyl ether can be produced by a known method. For example, such polyoxyethylene-polyoxypropylene random copolymer dialkyl ether can be obtained by subjecting ethylene oxide and propylene oxide to addition polymerization with a compound having a hydroxyl group, and then subjecting halogenated alkyl to an ether reaction in the presence of an alkali catalyst.

The incorporated amount of (C) polyoxyethylene-polyoxypropylene random copolymer dialkyl ether is preferably 10% to 60% by mass, and particularly preferably 20% to 40% by mass, with respect to the total mass of the oil-in-water emulsion composition (1). If the incorporated amount is less than 10% by mass, a fine emulsion is hardly obtained at a temperature of 70° C. or lower. On the other hand, if the incorporated amount exceeds 60% by mass, a stable oil-in-water emulsion composition may not be obtained when the composition is used for a cosmetic product or the like.

(D) Oil-soluble Drug

The type of an (D) oil-soluble drug used as an active ingredient in the oil-in-water emulsion composition of the present invention is not particularly limited, as long as it is an ingredient that can be dissolved in oil that is generally incorporated into pharmaceutical products, cosmetic products, and the like. Moreover, an amphipathic drug that is soluble in oil may also be used. Specific examples of such oil-soluble drug include an emollient agent, a skin-whitening agent, a skin roughness-preventing agent, an ultraviolet absorber, an anti-inflammatory agent, vitamins, and an antioxidant. In the present invention, one or more types are preferably selected from the aforementioned agents.

As an ingredient of (D) oil-soluble drug, a ceramide or ceramide analog as an emollient agent are particularly preferably incorporated. Since the oil-in-water emulsion composition of the present invention can stably incorporate such ceramide or ceramide analog, the effect of incorporating such ceramide or ceramide analog can be sufficiently obtained. Thus, for example, when the oil-in-water emulsion composition of the present invention is used for cosmetic products, it brings on elasticity and a refreshing feeling during use.

Ceramide is one type of sphingolipid, and it is a compound in which sphingosine binds to fat via an amide bond. Examples of such ceramide include N-(ω-acyloxy)acylsphingosine, N-acylsphingosine, N-acylphytosphingosine, N-(α-hydroxy)acylsphingosine (consisting of sphingosines containing 18 and 20 carbon atoms and α-oxyacids containing 24 to 28 carbon atoms), N-(α-hydroxy)acylsphingosine (consisting of sphingosines containing 17 and 18 carbon atoms and α-oxypalmitic acids), N-[ω-(α-hydroxy)acyloxy] acylsphingosine, and N-(α-hydroxy)acylphytosphingosine. These ceramides are all known lipid components derived from epidermal cells existing in the nature. In addition, the ceramide analog has a structure similar to that of the ceramide. Examples of such ceramide analog include (phytosteryl/decyltetradecyl) N-myristolylmethyl-β-alaninate (ELDEW (registered trade mark) APS-307; manufactured by Ajinomoto Co., Inc.), di(cholesteryl, behenyl, octyldodecyl) N-lauroyl-L-glutamate (ELDEW (registered trade mark) CL-301; manufactured by Ajinomoto Co., Inc.), di(cholesteryl, octyldodecyl) N-lauroyl-L-glutamate (ELDEW (registered trade mark) CL-202; manufactured by Ajinomoto Co., Inc.), di(phytosteryl, 2-octyldodecyl) N-lauroyl-L-glutamate (ELDEW (registered trade mark) PS-203; manufactured by Ajinomoto Co., Inc.), and di(phytosteryl, behenyl, 2-octyldodecyl) N-lauroyl-L-glutamate (ELDEW (registered trade mark) PS-304; manufactured by Ajinomoto Co., Inc.).

In addition, specific examples of other (D) oil-soluble drugs include: skin-whitening agents such as Biota orientalis, L-ascorbyl dipalmitate, L-ascorbate-2-glucoside, 2-O-ethylascorbic acid, 3-O-ethylascorbic acid, and tranexamic acid; skin roughness-preventing agents such as acetylsphinganine; ultraviolet absorbers such as octyl methoxycinnamate; anti-inflammatory agents such as stearyl glycyrrhetinate and peppermint oil; vitamins such as retinol, vitamin A and a derivative thereof (for example, vitamin A palmitate), an oil-soluble vitamin B derivative such as vitamin B6 palmitate, vitamin D and a derivative thereof, vitamin E and a derivative thereof (for example, vitamin E acetate), vitamin K and a derivative thereof, and vitamin H; and antioxidants such as coenzyme Q10 and butylhydroxytoluene.

The incorporated amount of (D) oil-soluble drug is preferably 0.0001% to 10% by mass, and particularly preferably 0.001% to 5% by mass, with respect to the total mass of the oil-in-water emulsion composition (1). If the incorporated amount is less than 0.0001% by mass, the usefulness of such oil-soluble drug may not be sufficiently exhibited. On the other hand, if the incorporated amount exceeds 10% by mass, the oil-soluble drug may not be stably maintained.

(E) Oil (E) Oil used in the oil-in-water emulsion composition of the present invention is oil other than the (D) oil-soluble drug. In general, the type of such oil used herein is not particularly limited, as long as it is used for cosmetic products and the like. All of liquid oils and fats, solid oils and fats, waxes, hydrocarbon oil, higher fatty acid, higher alcohol, synthetic ester oil, silicon oil, and the like can be used.

Examples of liquid oil include avocado oil, camellia oil, turtle oil, macadamia nut oil, corn oil, mink oil, olive oil, rapeseed oil, egg oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, paulownia oil, Japanese tung oil, jojoba oil, germ oil, and triglycerin.

Examples of solid oil include cacao butter, coconut oil, horse fat, hardened coconut oil, palm oil, beef tallow, mutton tallow, hardened beef tallow, palm kernel oil, pork tallow, beef bone tallow, Japan wax kernel oil, hardened oil, heatsfoot oil, Japan wax, and hardened castor oil.

Examples of waxes include beeswax, candelilla wax, cotton wax, carnauba wax, bayberry wax, Chinese wax, spermacetim, montan wax, rice bran wax, lanolin, kapok wax, lanolin acetate, liquid lanolin, sugar cane wax, isopropyl lanolate, hexyl laurate, reduced lanolin, jojoba wax, hard lanolin, shellac wax, POE lanoline alcohol ether, POE lanoline alcohol acetate, POE cholesterol ether, lanolin fatty acid polyethylene glycol, and POE hydrogenated lanolin alcohol ether.

Examples of hydrocarbon oils include liquid paraffin, ozokerite, squalane, pristane, paraffin, ceresin, squalene, petrolatum, and microcrystalline wax.

Examples of higher fatty acids include lauric acid, myristic acid, palmitic acid, stearic acid, behenic acid, oleic acid, undecylenic acid, tolic acid, isostearic acid, linoleic acid, linolenic acid, eicosapentaenoic acid (EPA), and docosahexaenoic acid (DHA).

Examples of higher alcohols include linear alcohols such as lauryl alcohol, cetyl alcohol, stearyl alcohol, behenyl alcohol, myristyl alcohol, oleyl alcohol, and cetostearyl alcohol; branched-chain alcohols such as monostearyl glycerin ether (batylalcohol), 2-decyltetradecynol, lanolin alcohol, cholesterol, phytosterol, hexyldodecanol, isostearyl alcohol, and octyldodecanol.

Examples of synthetic ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentylglycol dicaprate, diisostearyl malate, glyceryl di-2-heptylundecanoate, trimethylolpropane tri-2-ethylhexanoate, trimethylolpropane triisostearate, pentaerythritol tetra-2-ethylhexanoate, glyceryl tri(2-ethylhexanoate), glyceryl trioctanoate, glyceryl triisopalmitate, trimethylolpropane triisostearate, cetyl 2-ethylhexanoate, 2-ethylhexyl palmitate, glyceryl trimyristate, glyceride tri-2-heptylundecanoate, castor oil fatty acid methyl ester, oleyl oleate, acetoglyceride, 2-heptylundecyl palmitate, diisobutyl adipate, 2-octyldodecyl ester N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of silicone oil include linear polysiloxanes such as dimethylpolysiloxane, methylphenylpolysiloxane, and diphenylpolysiloxane; cyclic polysiloxanes such as octamethylcyclotetrasiloxane, decamethylcyclopentasiloxane, and dodecamethylcyclohexasiloxane; silicon resin forming three-dimensional network structure; silicone rubber; various kinds of modified polysiloxanes such as amino modified polysiloxane, polyether modified polysiloxane, alkyl modified polysiloxane, and fluorine modified polysiloxane; and acrylic silicones.

Among the above (E) oils, the oil-in-water emulsion composition of the present invention particularly preferably comprises a higher fatty acid containing 8 to 20 carbon atoms and/or a higher alcohol containing 8 to 20 carbon atoms. Moreover, the present oil-in-water emulsion composition preferably comprises isostearic acid as such higher fatty acid, or isostearyl alcohol as such higher alcohol.

The incorporated amount of (E) oil is preferably 5% to 25% by mass, and particularly preferably 8% to 20% by mass, with respect to the total mass of the oil-in-water emulsion composition (1). If the incorporated amount is less than 5% by mass, the oil-soluble drug may not be stably maintained. On the other hand, if the incorporated amount exceeds 25% by mass, it may cause poor feeling during use, such as stickiness, when the composition is used for a cosmetic product or the like.

(F) Water

The incorporated amount of (F) water is preferably 10% to 80% by mass, and particularly preferably 20% to 60% by mass, with respect to the total mass of the oil-in-water emulsion composition (1). If the incorporated amount is less than 10% by mass, there may be a case in which an oil-in-water emulsion composition cannot be obtained. On the other hand, if the incorporated amount exceeds 80% by mass, the incorporated amounts of the components (A) to (E) are relatively decreased. As a result, the usefulness of the oil-soluble drug may not be sufficiently exhibited, or a desired feeling during use that is characteristic for the oil-in-water emulsion composition may not be obtained.

Furthermore, it is also possible to incorporate any given aqueous component, as well as (F) water, to the oil-in-water emulsion composition (1) of the present invention. The type of such aqueous component is not particularly limited, as long as it is a component having water or an aqueous solvent as a main medium. Components that are generally used for cosmetic products, pharmaceutical products, and the like, may be incorporated within a range that does not affect stability. Examples of such aqueous component include: water; monoalcohols such as ethyl alcohol and isopropyl alcohol; polyhydric alcohols such as propylene glycol, 1,3-butylene glycol, dipropylene glycol, polyethylene glycol, glycerin, diglycerin, and polyglycerin; and plant extracts such as aloe vera, hamamelis, cucumber, lemon, lavender, and rose. These aqueous components may be used singly or in combination of two or more types. The incorporated amount of such aqueous component is, as a total mass with water, preferably 10% to 80% by mass, and particularly preferably 20% to 60%, with respect to the total mass of the oil-in-water emulsion composition (1).

Production Method

The oil-in-water emulsion composition (1) according to the present invention is constituted with the components (A) to (F). Hereafter, a method for producing the oil-in-water emulsion composition (1) of the present invention will be described.

1) Oil components that are the components (A) to (E) are dissolved or dispersed at a temperature of 70° C. or higher. At this moment, a layered gel structure is formed with (A) polyoxyethylene phytosterol and (B) glycerin fatty acid diester, and the obtained oil component mixture contains such layered gel structure.

2) While stirring the system at a constant temperature of 70° C. or higher, an aqueous component containing (F) water is gradually added and the mixture is emulsified. As a result, the obtained oil-in-water emulsion composition (1) contains a layered gel structure constituted with the components (A) and (B) in the emulsion particles thereof. In addition, a part of these emulsion particles is prepared in the form of capsule in which an internal phase oil is coated with the layered gel structure. Thus, (D) oil-soluble drug is extremely stably maintained in the internal oil phase.

In the oil-in-water emulsion composition (1) of the present invention, a layered gel structure formed with (A) polyoxyethylene phytosterol and (B) glycerin fatty acid diester is one type of aggregate formed with a surfactant and an amphipathic substance. Such layered gel structure has a crystal structure characterized in that the bimolecular membranes of the surfactant and amphipathic substance are arranged in laminae in the long-period structure, and in that the hydrophobic groups of the surfactant and amphipathic substance are arranged in a hexagonal form on the short surface side. A hydrophobic group rotates around the long axis thereof. However, differing from a liquid crystal structure, it does not become thermalized freely. In addition, it has been known that a large amount of water exists between hydrophilic groups (for example, see Shoji Fukushima, "Cetyl alcohol no butsuri kagaku (Physical chemistry of cetyl alcohol)," Fragrance Journal Ltd., Chapter 6, pp. 76-88).

The presence or absence of a layered gel structure can be determined by a conventionally known method. For example, it can be carried out by an X-ray scattering method. When an X-ray scattering measurement is performed on a composition containing a layered gel structure, repeated peaks derived from long surface intervals, which are similar to a lamellar structure, are generally obtained in a small-angle region, and at the same time, a single sharp peak derived from a hexagonal system on the short surface side is obtained in a wide-angle region. Moreover, according to a differential scanning calorimetric (DSC) measurement, an endothermic peak attended with the fusion of a crystal structure containing a layered gels structure is observed, and using such peak, it is also possible to analyze the crystal structure.

Moreover, in the method for producing the oil-in-water emulsion composition of the present invention, a phase inversion temperature in the system is decreased by incorporating therein (C) polyoxyethylene-polyoxypropylene random copolymer dialkyl ether. Thus, even if the oil-in-water emulsion composition of the present invention is emulsified at a temperature around 70° C. or a temperature higher than 70° C., an oil-in-water emulsion composition having fine emulsion particles with the internal oil phase having a particle diameter of 50 to 1,000 nm can be produced.

Furthermore, in the oil-in-water emulsion composition (1) of the present invention, a layered gel structure formed with (A) polyoxyethylene phytosterol and (B) glycerin fatty acid diester is formed around the interface of an emulsion particle. Thus, a capsule in which an internal phase oil is coated with the layered gel structure can be prepared. Accordingly, an oil-soluble drug incorporated in the internal oil phase can be extremely stably maintained, for example.

Using the thus prepared oil-in-water emulsion composition (1) as a base material, such emulsion composition is diluted with an aqueous formulation and is uniformly dispersed, so that an oil-in-water emulsion composition (2) having excellent stability can be obtained. Herein, the oil-in-water emulsion composition (2) can also have a fine emulsion particle size, which can be achieved by the oil-in-water emulsion composition (1). The thus prepared oil-in-water emulsion composition (2) can be preferably used as, particularly a cosmetic product. In such a case, other components that are generally used in cosmetic products, pharmaceutical products, and the like, can be incorporated into the aqueous formulation.

Examples of other components include water, a water-soluble component, a moisturizing agent, an oil, a surfactant, a thickener, various types of powders, a pigment, a film-forming agent, a pH adjuster, an anti-fading agent, an antifoaming agent, an antiseptic, a drug, and a flavor. These components can be appropriately incorporated into the aqueous formulation in a range that does not impair the effects of the present invention.

Examples of a water-soluble component that can be used herein include sugars such as sorbitol, maltitol and sucrose, electrolytes such as sodium chloride, magnesium chloride and sodium lactate, as well as monoalcohols, polyhydric alcohols, and plant extracts, which are exemplified as the aforementioned aqueous components.

Examples of a moisturizing agent include protein, mucopolysaccharide, collagen, and elastin.

Examples of an oil include animal oil, plant oil, and synthetic oil. Regardless of the states of oils, such as solid oil, semi-solid oil, liquid oil, and volatile oil, more specific examples of such oil include hydrocarbon oil, oils and fats, waxes, hardened oil, ester oil, fatty acid, higher alcohol, silicon oil, fluorine oil, a lanolin derivative, and an oil gelator.

Any type of surfactant can be used, as long as it is generally used for cosmetic products.

Examples of a thickener include water-soluble polymers such as guar gum, sodium chondroitin sulfate, sodium hyaluronate, gum Arabic, sodium alginate, carrageenan, methylcellulose, hydroxyethylcellulose, carboxymethylcellulose, a carboxy vinyl polymer, polyvinyl alcohol, polyvinylpyrrolidone, and sodium polyacrylate.

Powders are not particularly limited by forms such as platy, fusiform, acicular or spherical, particle structures such as porous or imperforate, particle diameter, and the like. Various types of powders, such as inorganic powders, photoluminescent powders, laminate film powders, organic powders, pigment powders, and composite powders, can be used. Further, these powders can be surface-treated by a known method using a fluorine compound, a silicon oil, a metallic soap, a wax, a surfactant, oils and fats, hydrocarbon, and the like.

As a film-forming agent, emulsion polymers such as a (meth)acrylic acid-alkyl copolymer can be used. As a pH adjuster, α-hydroxy acids such as lactic acid and citric acid and the salts thereof, edetate, and the like can be used. As an antioxidant, α-tocopherol, butylhydroxytoluene, ascorbic acid, and the like can be used. As an antiseptic, p-hydroxybenzoic ester, phenoxyethanol, and the like can be used.

The form of a cosmetic product is not particularly limited. Various forms such as a solution, a solubilized product, an emulsion, an oil, an aqueous product, and a two-layer- or three-layer-type product having two or more of the aforementioned product form can be adopted. Examples of a cosmetic product include a skin care product, a hair care product, and a product for make up. Of these, a skin care product is preferable. In order to effectively achieve the effects of the incorporated active ingredients, when a skin care product is prepared, it is particularly preferably an aqueous product such as a lotion, a milky lotion, or a cream. When the oil-in-water emulsion composition according to the present invention is incorporated into such cosmetic product, the type of the cosmetic product is appropriately selected depending on the form.

EXAMPLES

Hereinafter, the present invention will be more specifically described in the following examples. However, these examples are not intended to limit the scope of the present invention.

First, the present inventors have prepared an oil-in-water emulsion composition having the below formulation. Thereafter, a TEM (transmission electron microscope) image of a frozen replica was photographed. Thus, the fine structure of the oil-in-water emulsion composition was analyzed. A transmission electron microscope H-7000 (manufactured by Hitachi, Ltd.) was used for such TEM photographing.

| Test Example 1-1: oil-in-water emulsion composition | amount (mass %) |
|---|---|
| Polyoxyethylene (30 moles) phytosterol ester | 5.38 |
| Isostearic acid | 10.75 |
| Isostearyl alcohol | 12.90 |
| Glyceryl di-2-heptylundecanoate | 6.45 |
| Polyoxyethylene (14 moles) polyoxypropylene (7 moles) random copolymer dimethyl ether | 32.26 |
| Purified water | Balance |

Production Method

Polyoxyethylene (30 moles) phytosterol ester, isostearic acid, isostearyl alcohol, glyceryl di-2-heptylundecanoate, and polyoxyethylene (14 moles) polyoxypropylene (7 moles) random copolymer dimethyl ether were dissolved by heating at 70° C., then stirred and mixed. Subsequently, while the obtained mixture was stirred at a constant temperature of 70° C., purified water was gradually added thereto for emulsification, so as to obtain the oil-in-water emulsion composition of Test Example 1-1.

Figure 1:
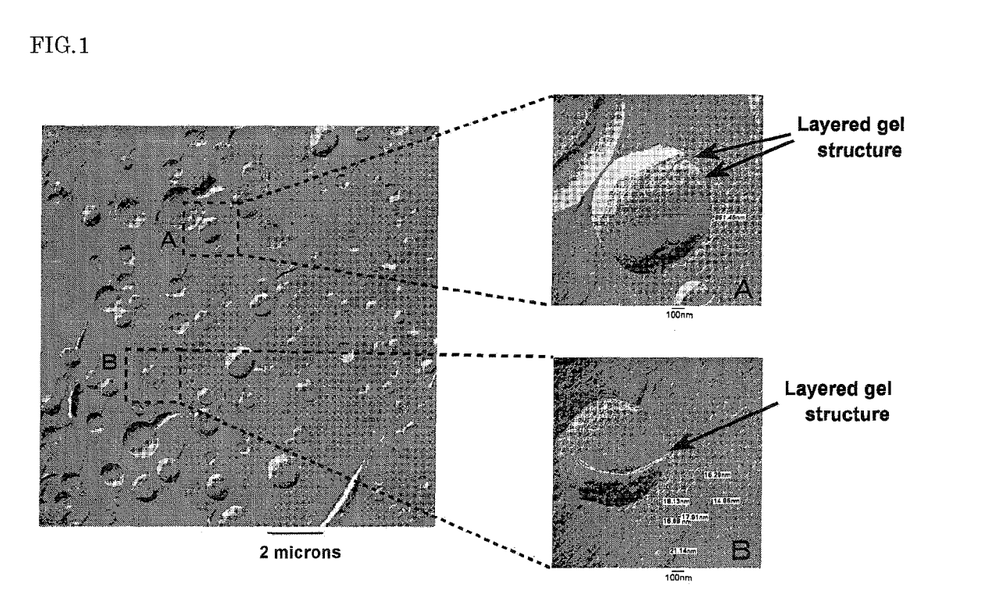
FIG. 1 shows photographs of a transmission electron microscope (TEM) of the oil-in-water emulsion composition (Test Example 1-1) according to the present invention.
Figure 2:
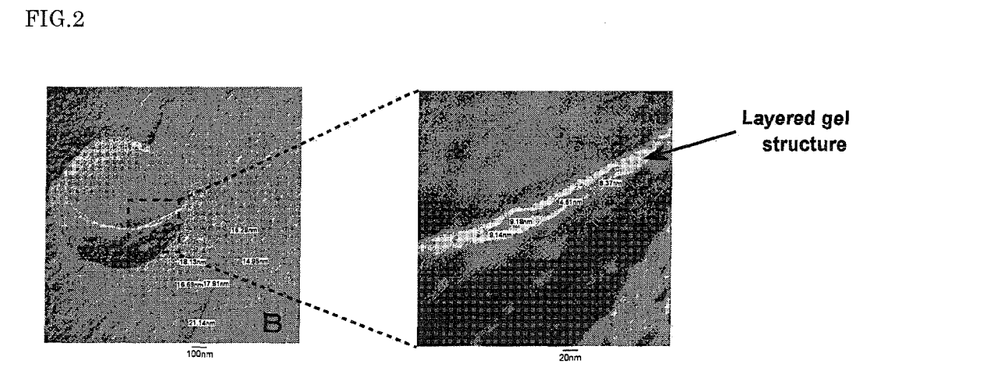
FIG. 2 shows photographs of a transmission electron microscope (TEM) of the oil-in-water emulsion composition (Test Example 1-1) according to the present invention.

TEM photographs of the oil-in-water emulsion composition of Test Example 1-1 are shown in FIG. 1, and enlarged TEM photographs of several emulsion particles are shown in FIG. 2.

As shown in FIG. 1, it is found that fine emulsion particles with a particle diameter of approximately 50 to 1,000 nm were formed in the oil-in-water emulsion composition of Test Example 1-1. In the same figure, in several emulsion particles (in particular, A and B in FIG. 1), there can be confirmed the presence of layered gel structures, which were probably broken in each of the layers during the production of the frozen replica sample. In addition, in the same figure, it is found that such layered gel structure is present such that it covers the emulsion particles as a whole, and thus that capsular emulsion particles containing a coated internal phase oil are formed.

Moreover, in FIG. 2, the thickness of the layered structure of the emulsion particle outer membrane is found to be approximately 9 nm. Accordingly, such layered structure is assumed to correspond to the bimolecular membrane of lamellar structure formed with a surfactant and an amphipathic substance.

Next, in order to further analyze the formation of such layered gel structure, a basic compositor as Test Example 1-1, a composition prepared by mixing oil components in the basic composition except purified water as Test Example 1-2, and a composition prepared by further removing polyoxyethylene (14 moles) polyoxypropylene (7 moles) random copolymer dimethyl ether from the same above oil component mixture as Test Example 1-3 were prepared. Each of the compositions were analyzed by a small-angle X-ray scattering measurement. Such small-angle X-ray scattering measurement was carried out using SAXSESS (manufactured by PANalytical).

Figure 3:
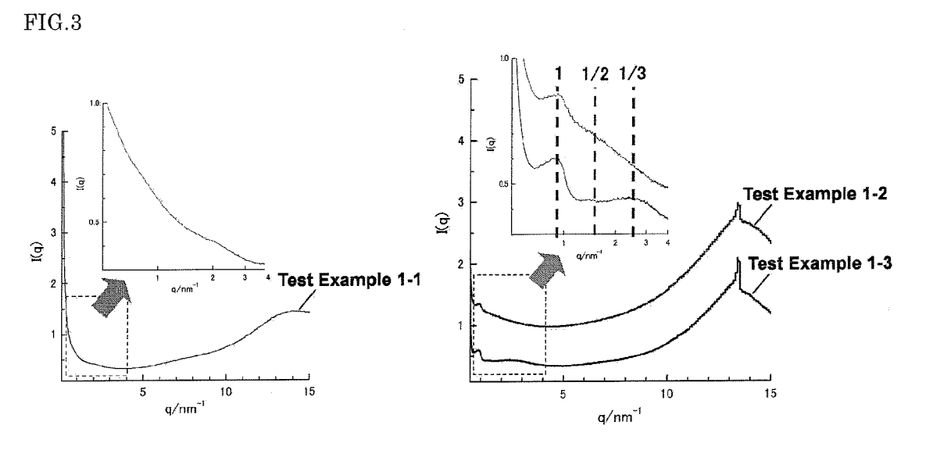
FIG. 3 shows the results of the X-ray scattering measurement of the oil-in-water emulsion compositions (Test Examples 1-1, 1-2 and 1-3) according to the present invention.

The results of the X-ray scattering measurement of the compositions of Test Examples 1-1 to 1-3 are shown in FIG. 3.

In FIG. 3, with regard to both Test Examples 1-2 and 1-3, a single sharp peak derived from a hexagonal system on the short surface side was observed in a wide-angle region, and repeated peaks derived from the long surface intervals of a lamellar structure were observed in a small-angle region. Thus, the presence of a layered gel structure was confirmed in the compositions of both Test Examples 1-2 and 1-3. Herein, the presence of the polyoxyethylene (14 moles) polyoxypropylene (7 moles) random copolymer dimethyl ether did not affect the surface intervals of the lamellar structure in the small-angle region. This fact suggests that the component did not directly influence on the formation of a layered gel structure.

On the other hand, in the oil-in-water emulsion composition of Test Example 1-1, a peak derived from a layered gel structure disappeared. This is because an oil phase containing a gel structure became spherical due to emulsification and because anisotropy caused by such layered structure disappeared. Thus, it is considered that the layered gel structure was still present in the oil phase.

Furthermore, in order to analyze in detail the constituents of such layered gel structure, a composition prepared by removing isostearic acid from the oil component mixture of the Test Example 1-2 (Test Example 1-4), a composition prepared by removing isostearyl alcohol from the oil component mixture of the Test Example 1-2 (Test Example 1-5), and a composition prepared by removing glyceryl di-2-heptylundecanoate from the oil component mixture of the Test Example 1-2 (Test Example 1-6) were prepared. Each of the compositions were analyzed by the above X-ray scattering measurement.

Figure 4:
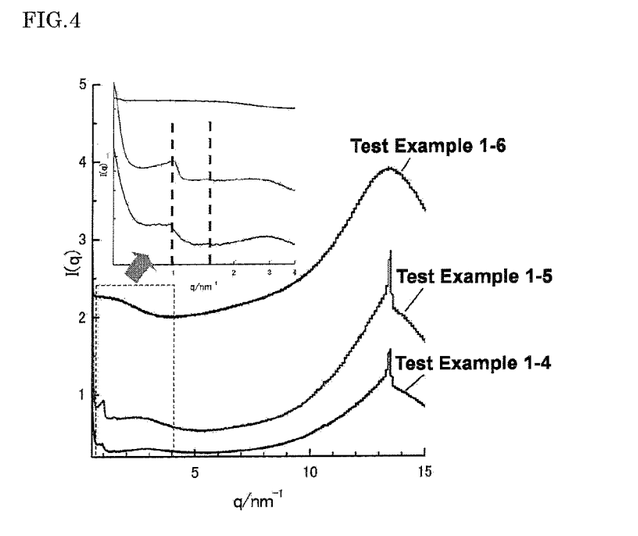
FIG. 4 shows the results of the X-ray scattering measurement of the oil-in-water emulsion compositions (Test Examples 1-4, 1-5 and 1-6) according to the present invention.

The results of the X-ray scattering measurement of the compositions of Test Examples 1-4 to 1-6 are shown in FIG. 4.

In FIG. 4, with regard to both Test Examples 1-4 and 1-5, from which isostearic acid and isostearyl alcohol were removed, respectively, a single sharp peak was observed in a wide-angle region and repeated peaks were observed in a small-angle region, as in the case of the above test examples. Thus, it is confirmed that a layered gel structure was formed in each composition.

In contrast, in the oil-in-water emulsion composition of Test Example 1-6, from which glyceryl di-2-heptylundecanoate was removed, a peak became broad in the wide-angle region, and repeated peaks disappeared from the small-angle region. Thus, it is clear that a layered gel structure was not formed, and that glyceryl di-2-heptylundecanoate was directly associated with the formation of such layered gel structure.

From the above results, it is understood that layered gel structures observed in Test Example 1-2 and Test Example 1-3 were each formed with polyoxyethylene (30 moles) phytosterol ester and glyceryl di-2-heptylundecanoate, and that these components were essential for the formation of the layered gel structure.

Thereafter, in order to analyze the influence of polyoxyethylene (14 moles) polyoxypropylene (7 moles) random copolymer dimethyl ether on the production of an oil-in-water emulsion composition, the present inventors have performed a measurement with a differential scanning calorimeter (DSC) on various types of oil-in-water emulsion compositions, in which the incorporated amount of the component was changed as appropriate. Using the oil-in-water emulsion composition of Test Example 1-1 as a basic composition, the following oil-in-water emulsion compositions were prepared: a composition in which the concentration of the polyoxyethylene (14 moles) polyoxypropylene (7 moles) random copolymer dimethyl ether was set at 0 (zero) (Test Example 2-1); a composition in which the same above concentration was set at 10% by mass (Test Example 2-2); a composition in which the same above concentration was set at 20% by mass (Test Example 2-3); and a composition in which the same above concentration was set at 32% by mass (Test Example 2-4), and thereafter, they were used in the subsequent test. In addition, the DSC measurement was carried out using DSC8230D (manufactured by Rigaku Denki Co., Ltd), under conditions consisting of 20 mg of sample, a temperature-increasing rate of 2 K/min, and a measurement temperature range of 30° C. to 110° C.

Figure 5:
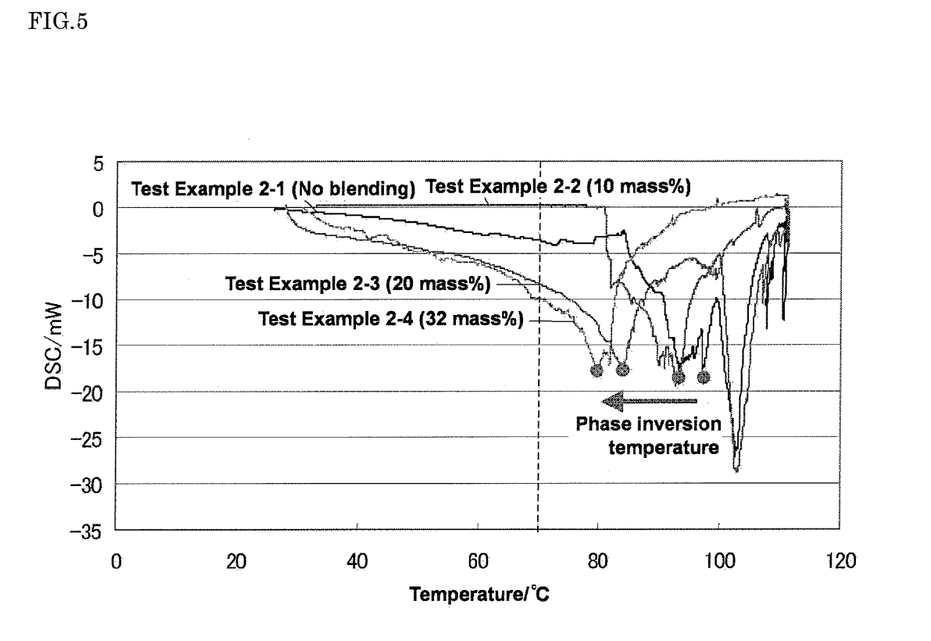
FIG. 5 shows the results of the differential scanning calorimetric (DSC) measurement of the oil-in-water emulsion compositions (Test Examples 2-1 to 2-4) according to the present invention.

The DSC measurement results of the samples of Test Examples 2-1 to 2-4 are shown in FIG. 5. In addition, the correlation between the mixed amount of polyoxyethylene (14 moles) polyoxypropylene (7 moles) random copolymer dimethyl ether and a phase inversion temperature, which was obtained based on the results shown in FIG. 5, is shown in FIG. 6.

Figure 6:
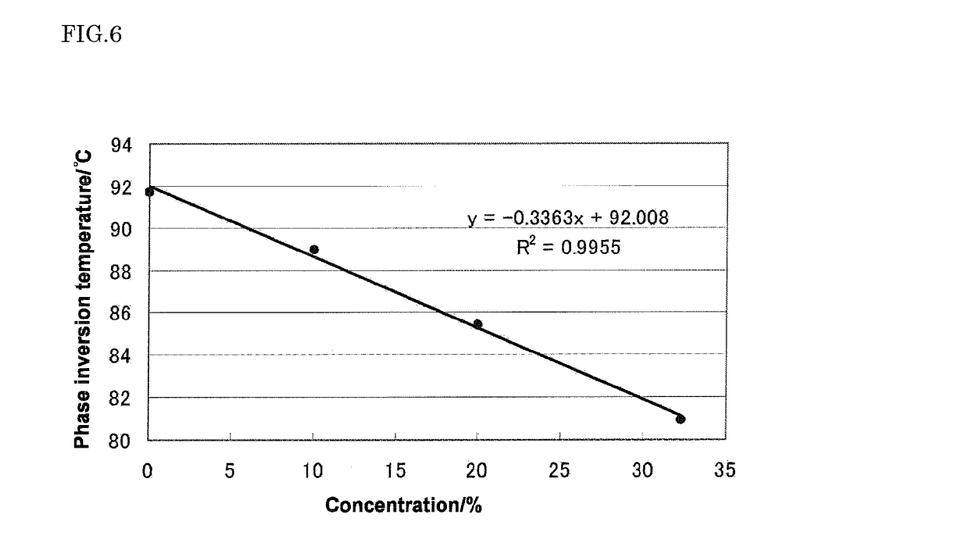
FIG. 6 is a view showing the correlation between the incorporated amount of (C) polyoxyethylene (14 moles) polyoxypropylene (7 moles) random copolymer dialkyl ether in the oil-in-water emulsion composition according to the present invention and a phase inversion temperature.

From the results shown in FIGS. 5 and 6, it is clear that the phase inversion temperature of each sample was decreased, as the incorporated amount of the polyoxyethylene (14 moles) polyoxypropylene (7 moles) random copolymer dimethyl ether was increased. From such results, it is understood that the addition of the polyoxyethylene (14 moles) polyoxypropylene (7 moles) random copolymer dimethyl ether enables easy preparation of an oil-in-water emulsion composition at an emulsification temperature around 70° C.

Subsequently, using the oil-in-water emulsion composition of Test Example 1-1 as a base material, the present inventors have attempted to prepare a lotion (Test Example 3-1) by diluting and uniformly dispersing the base material in an aqueous formulation. The final composition of the ingredients of the lotion of Test Example 3-1 is described below. Moreover, the lotion of Test Example 3-1 was photographed using TEM (transmission electron microscope) in the same manner as that in the above test, and the emulsified state was analyzed.

| Test Example 3-1: lotion | amount (mass %) |
|---|---|
| (Oil-in-water emulsion composition) | |
| Polyoxyethylene (30 moles) phytosterol ester | 0.3 |
| Isostearic acid | 0.5 |
| Isostearyl alcohol | 0.6 |
| Glyceryl di-2-heptylundecanoate | 0.25 |
| Polyoxyethylene (14 moles) polyoxypropylene (7 moles) random copolymer dimethyl ether | 1.5 |
| Purified water | 1.5 |
| (Aqueous formulation) | |
| Ethanol | 5.6 |
| 1,3-butylene glycol | 13.0 |
| Methylparaben | 0.15 |
| Purified water | Balance |

(Production Method)

Polyoxyethylene (30 moles) phytosterol ester, isostearic acid, isostearyl alcohol, glyceryl di-2-heptylundecanoate, and polyoxyethylene (14 moles) polyoxypropylene (7 moles) random copolymer dimethyl ether were dissolved by heating at 70° C., then stirred and mixed. Subsequently, while the obtained mixture was stirred at a constant temperature of 70° C., purified water was gradually added thereto for emulsification, so as to obtain an oil-in-water emulsion composition. The obtained oil-in-water emulsion composition was further added to an aqueous formulation containing ethanol, 1,3-butylene glycol, and methylparaben, and the mixture was then uniformly dispersed by stirring, so as to obtain the lotion of Test Example 3-1.

A summary of the TEM photographs of the oil-in-water emulsion composition of Test Example 1-1 and the lotion of Test Example 3-1 is shown in FIG. 7.

From FIG. 7, almost no changes were found in terms of the size of an emulsion particle before and after the addition of the emulsion composition into the aqueous formulation. Thus, it was found that a fine emulsion particle diameter was maintained even in a case in which the composition was diluted with a large amount of aqueous formulation. Also, from the same figure, it became clear that, even in the case of the lotion of Test Example 3-1, emulsion particles were maintained in the form of capsule coated with a layered gel structure.

Furthermore, the present inventors have produced lotions comprising various types of oil-soluble drugs in the same manner as that of the Test Example 3-1, and then evaluated such lotions in terms of emulsion particle diameter, feeling during use, and emulsion stability. The compositions of lotions used in the test and the evaluation results are shown in Table 1 below. The following evaluation standards were applied.

Feeling During Use

With regard to the feeling during use of the lotions of the respective test examples, 20 female panelists actually used the lotions, and then evaluated feeling during use in accordance with the following standards.

⊚: 16 or more panelists, who felt that the lotion fitted comfortably in the skin and it penetrated therein.

O: 10 to 15 panelists, who felt that the lotion fitted comfortably in the skin and it penetrated therein.

Δ: 6 to 9 panelists, who felt that the lotion fitted comfortably in the skin and it penetrated therein.

X: 5 or less panelists, who felt that the lotion fitted comfortably in the skin and it penetrated therein.

Emulsion Particle Diameter

The lotions of the respective test examples were preserved under temperature conditions of 0° C., a room temperature, 37° C., and 50° C., for 1 month. Thereafter, emulsion particle diameter was measured by a light scattering method. F-PAR-1000 (manufactured by Otsuka Electronics Co., Ltd.) was used as a device.

Emulsion Stability

The lotions of the respective test examples were preserved under temperature conditions of 0° C., a room temperature, 37° C., and 50° C., for 1 month. Thereafter, emulsion stability was evaluated in accordance with the following standards.

⊚: Abnormality such as separation or change in appearance was not observed at all.

O: Separation was observed to a small extent, but it was retuned to the original state by stirring.

Δ: Separation was observed.

X: Separation and creaming were observed.

TABLE 1

| | Test Example 4-1 | Test Example 4-2 | Test Example 4-3 | Test Example 4-4 |
|---|---|---|---|---|
| (A) POE(30) phytosterol ester | 0.3 | 0.3 | 0.3 | 0.3 |
| (B) Glyceryl di-2-heptylundecanoate | 0.15 | 0.25 | 0.25 | 0.15 |
| (C) POE(14)POP(7)dimethyl ether (random) | 1.5 | 1.5 | 1.5 | 1.5 |
| (D) Isostearic acid | 0.5 | 0.4 | 0.5 | 0.5 |
| (D) Isostearyl alcohol | 0.6 | 0.6 | 0.6 | 0.6 |
| (E) Biota orientalis | 0.1 | — | — | — |
| (E) Acetylsphinganine | — | 0.1 | — | — |
| (E) Coenzyme Q10 | — | — | 0.01 | — |
| (E) Ethylhexyl methoxycinnamate | — | — | — | 0.1 |
| (F) Ion-exchange water | Balance | Balance | Balance | Balance |

TABLE 1-continued

|  | Test Example 4-1 | Test Example 4-2 | Test Example 4-3 | Test Example 4-4 |
|---|---|---|---|---|
| Ethanol | 5.6 | 5.6 | 5.6 | 5.6 |
| 1,3-butylene glycol | 13.0 | 13.0 | 13.0 | 13.0 |
| Methylparaben | 0.15 | 0.15 | 0.15 | 0.15 |
| Evaluation Feeling during use | ◎ | ◎ | ◎ | ◎ |
| Emulsion particle diameter [nm] (0° C.) | 189 | 170 | 191 | 204 |
| Emulsion particle diameter [nm] (RT) | 218 | 185 | 195 | 206 |
| Emulsion particle diameter [nm] (37° C.) | 207 | 182 | 193 | 207 |
| Emulsion particle diameter [nm] (50° C.) | 203 | 173 | 189 | 204 |
| Emulsion stability (0° C.) | ◎ | ◎ | ◎ | ◎ |
| Emulsion stability (RT) | ○ | ○ | ○ | ○ |
| Emulsion stability (37° C.) | ○ | ○ | ○ | ○ |
| Emulsion stability (50° C.) | ○ | ○ | ○ | ○ |

Production Method

The components (A) to (E) were dissolved or dispersed at a temperature of 70° C. or higher. While stirring the reaction system at a constant temperature of 70° C. or higher, (F) water was gradually added to the oil component mixture, so as to emulsify it. The obtained emulsion composition was further added to an aqueous formulation containing ethanol, 1,3-butylene glycol, and methylparaben, and the mixture was then uniformly dispersed by stirring, so as to obtain the lotions of various types of test examples.

As shown in Table 1 above, in the case of the lotions of Test Examples 4-1 to 4-4, in which various types of (E) oil-soluble drugs such as Biota orientalis, acetylsphinganine, coenzyme Q10, and ethylhexyl methoxycinnamate had been incorporated, since a layered gel structure was formed in the system, extremely good feeling was obtained during use. Moreover, since (E) oil-soluble drug was extremely stably maintained in an internal oil phase because of such layered gel structure, it led to only a small change in emulsion particle diameter, and good emulsion stability was obtained over time.

Hereafter, Formulation Examples of cosmetic products, in which the oil-in-water emulsion composition according to the present invention is used, will be described, and thus, the present invention will be explained more in detail. However, these examples are not intended to limit the scope of the present invention. It is to be noted that numerical values in each Formulation Example are indicated with "% by mass" with respect to the total mass of the final cosmetic product.

| Formulation Example 1: white lotion | amount (mass %) |
|---|---|
| (Oil-in-water emulsion composition) | |
| (1) Coenzyme Q10 | 0.03 |
| (2) Glyceryl di-2-heptylundecanoate | 0.25 |
| (3) Isostearic acid | 0.5 |
| (4) Isostearyl alcohol | 0.6 |
| (5) Polyoxyethylene (30 moles) phytosterol ester | 0.3 |
| (6) Polyoxyethylene (14 moles) polyoxypropylene (7 moles) random copolymer dimethyl ether | 1.5 |
| (7) Purified water | 1.5 |
| (Aqueous formulation) | |
| (8) Ethanol | 5.0 |
| (9) 1,3-butylene glycol | 7.0 |
| (10) Glycerin | 5.0 |
| (11) Diglycerin | 0.5 |
| (12) Methylparaben | 0.2 |
| (13) Purified water | Balance |

(Production Method)

The components (1) to (6) were dissolved by heating at 70° C., then stirred and mixed. While the mixture was stirred at a constant temperature of 70° C., the component (7) was gradually added thereto for emulsification, and as a result, an oil-in-water emulsion composition was obtained. The obtained oil-in-water emulsion composition was further added to an aqueous formulation containing the components (8) to (13), and they were then uniformly dispersed by stirring, so as to obtain a white lotion.

| Formulation Example 2: white lotion | amount (mass %) |
|---|---|
| (Oil-in-water emulsion composition) | |
| (1) Acetylsphinganine | 0.1 |
| (2) Glyceryl di-2-heptylundecanoate | 0.25 |
| (3) Isostearic acid | 0.4 |
| (4) Isostearyl alcohol | 0.6 |
| (5) Polyoxyethylene (30 moles) phytosterol ester | 0.3 |
| (6) Polyoxyethylene (14 moles) polyoxypropylene (7 moles) random copolymer dimethyl ether | 1.5 |
| (7) Purified water | 1.7 |
| (Aqueous formulation) | |
| (8) Ethanol | 6.0 |
| (9) 1,3-butylene glycol | 8.0 |
| (10) Glycerin | 4.0 |
| (11) Diglycerin | 0.3 |
| (12) Methylparaben | 0.1 |
| (13) Purified water | Balance |

(Production Method)

The components (1) to (6) were dissolved by heating at 70° C., then stirred and mixed. While the mixture was stirred at a constant temperature of 70° C., the component (7) was gradually added thereto for emulsification, and as a result, an oil-in-water emulsion composition was obtained. The obtained oil-in-water emulsion composition was further added to an aqueous formulation containing the components (8) to (13), and they were then uniformly dispersed by stirring, so as to obtain a white lotion.

| Formulation Example 3: white lotion | amount (mass %) |
|---|---|
| (Oil-in-water emulsion composition) | |
| (1) Octyl methoxycinnamate | 0.1 |
| (2) Glyceryl di-2-heptylundecanoate | 0.15 |
| (3) Isostearic acid | 0.5 |

-continued

| Formulation Example 3: white lotion | amount (mass %) |
|---|---|
| (4) Isostearyl alcohol | 0.6 |
| (5) Polyoxyethylene (30 moles) phytosterol ester | 0.3 |
| (6) Polyoxyethylene (14 moles) polyoxypropylene (7 moles) random copolymer dimethyl ether | 1.5 |
| (7) Purified water | 1.5 |
| (Aqueous formulation) | |
| (8) Ethanol | 5.5 |
| (9) 1,3-butylene glycol | 7.5 |
| (10) Glycerin | 4.5 |
| (11) Diglycerin | 1.0 |
| (12) Methylparaben | 0.2 |
| (13) Purified water | Balance |

(Production Method)

The components (1) to (6) were dissolved by heating at 70° C., then stirred and mixed. While the mixture was stirred at a constant temperature of 70° C., the component (7) was gradually added thereto for emulsification, and as a result, an oil-in-water emulsion composition was obtained. The obtained oil-in-water emulsion composition was further added to an aqueous formulation containing the components (8) to (13), and they were then uniformly dispersed by stirring, so as to obtain a white lotion.

| Formulation Example 4: milky lotion | amount (mass %) |
|---|---|
| (Oil-in-water emulsion composition) | |
| (1) Coenzyme Q10 | 0.01 |
| (2) Glyceryl di-2-heptylundecanoate | 0.15 |
| (3) Isostearic acid | 0.5 |
| (4) Isostearyl alcohol | 0.6 |
| (5) Polyoxyethylene (30 moles) phytosterol ester | 0.3 |
| (6) Polyoxyethylene (14 moles) polyoxypropylene (7 moles) random copolymer dimethyl ether | 1.5 |
| (7) Polyoxyethylene (17 moles) polyoxypropylene (4 moles) random copolymer dimethyl ether | 1.0 |
| (8) Vitamin E acetate | 0.01 |
| (9) Purified water | 1.5 |
| (Aqueous formulation) | |
| (10) Ethanol | 5.0 |
| (11) 1,3-butylene glycol | 5.0 |
| (12) Glycerin | 7.0 |
| (13) Diglycerin | 1.0 |
| (14) Polyethylene glycol | 2.0 |
| (15) Polyacrylic acid | 0.15 |
| (16) Xanthan gum | 0.2 |
| (17) Potassium hydroxide | 0.005 |
| (18) Sodium hexametaphosphate | 0.03 |
| (19) EDTA | 0.01 |
| (20) Phenoxy ethanol | 0.5 |
| (21) Purified water | Balance |

(Production Method)

The components (1) to (8) were dissolved by heating at 70° C., then stirred and mixed. While the mixture was stirred at a constant temperature of 70° C., the component (9) was gradually added thereto for emulsification, and as a result, an oil-in-water emulsion composition was obtained. The obtained oil-in-water emulsion composition was further added to an aqueous formulation containing the components (10) to (21), and they were then uniformly dispersed by stirring, so as to obtain an emulsion.

| Formulation Example 5: milky lotion | amount (mass %) |
|---|---|
| (Oil-in-water emulsion composition) | |
| (1) Polyoxyethylene (14 moles) polyoxypropylene (7 moles) random copolymer dimethyl ether | 1.25 |
| (2) Polyoxyethylene (30 moles) phytosterol ester | 0.75 |
| (3) (Phytosteryl/decyltetradecyl) N-myristolylmethyl-β-alaninate* | 1.0 |
| (4) Glyceryl di-2-heptylundecanoate | 0.5 |
| (5) Isostearic acid | 0.5 |
| (6) Purified water | 1.5 |
| (Aqueous formulation) | |
| (7) Purified water | 81.99 |
| (8) Citric acid | 0.01 |
| (9) Sodium citrate | 0.09 |
| (10) Trisodium hydrogen ethylenediaminetetraacetate | 0.01 |
| (11) Glycerin | 2.0 |
| (12) 1,3-butylene glycol | 5.0 |
| (13) Xanthan gum | 0.1 |
| (14) Ethanol | 5.0 |
| (15) Phenoxy ethanol | 0.3 |

*ELDEW (registered trade mark) APS-307: manufactured by Ajinomoto Co., Inc.

(Production Method)

The components (1) to (5) were dissolved by heating at 70° C., then stirred and mixed. While the mixture was stirred at a constant temperature of 70° C., the component (6) was gradually added thereto for emulsification, and as a result, an oil-in-water emulsion composition was obtained. The obtained oil-in-water emulsion composition was further added to an aqueous formulation containing the components (7) to (15), and they were then uniformly dispersed by stirring, so as to obtain an emulsion.

The emulsion obtained by the Formulation Example 5 was particularly excellent in terms of elasticity, and it brought on a refreshing feeling during use without stickiness.

Figure 8:
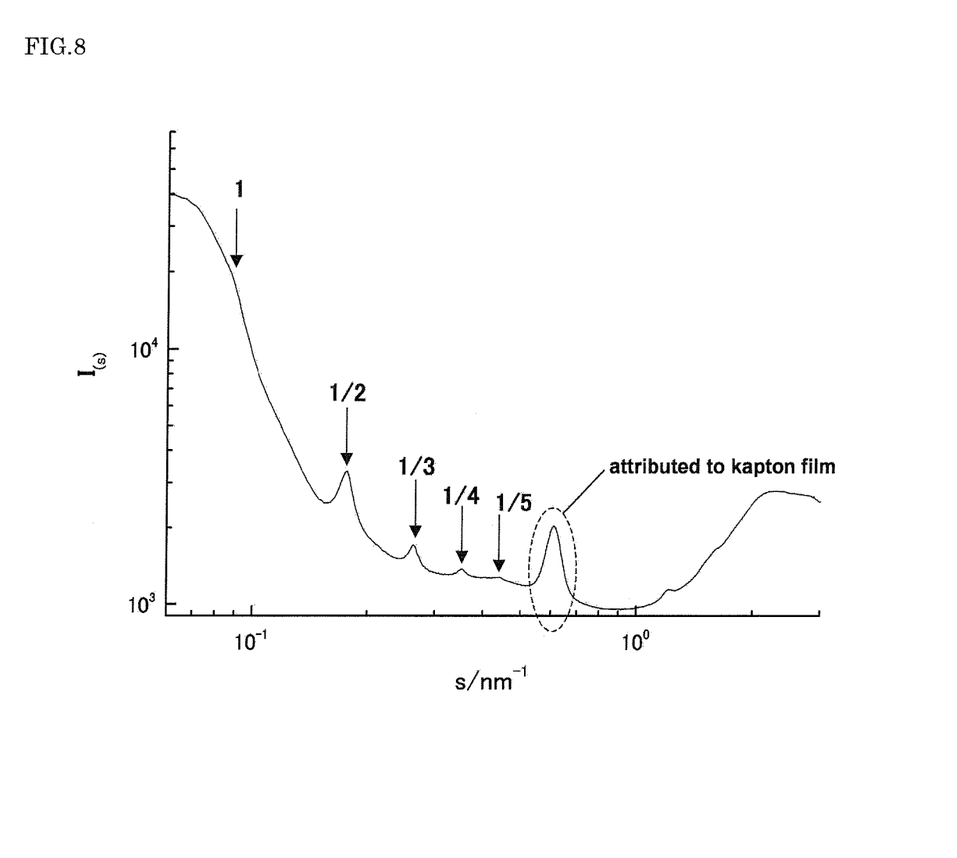
FIG. 8 shows the results of the X-ray scattering measurement of the oil-in-water emulsion composition (Formulation Example 5) according to the present invention.

Moreover, the oil-in-water emulsion composition of the Formulation Example 5 was subjected to a small-angle X-ray scattering measurement (SAXSESS: manufactured by PANalytical). The results of the X-ray scattering measurement are shown in FIG. 8. As shown in FIG. 8, repeated peaks derived from the long surface intervals of a lamellar structure were observed in the small angle region. Thus, it was confirmed that a layered gel structure was present in the oil-in-water emulsion composition.

What is claimed is:

1. An oil-in-water emulsion composition comprising;
   (A) a polyoxyethylene phytosterol,
   (B) a glycerin fatty acid diester,
   (C) a polyoxyethylene-polyoxypropylene random copolymer dialkyl ether,
   (D) an oil-soluble drug,
   (E) oil, and
   (F) water;
   wherein a layered gel structure having a crystal structure of bimolecular membranes composed of the components (A) and (B) is present in an emulsion particle in the emulsion composition.

2. The oil-in-water emulsion composition of claim 1, wherein at least a portion of the emulsion particles are in the form of a capsule composed of an internal oil phase coated with the layered gel structure.

3. The oil-in-water emulsion composition of claim 1 wherein the (C) polyoxyethylene-polyoxypropylene dialkyl ether random copolymer comprises a polyoxyethylene-polyoxypropylene dimethyl ether random copolymer.

4. The oil-in-water emulsion composition of claim 1, wherein the (D) oil-soluble drug is one or more selected from the group consisting of an emollient agent, a skin-whitening agent, a skin roughness-preventing agent, an ultraviolet absorber, an anti-inflammatory agent, vitamins, and an antioxidant.

5. The oil-in-water emulsion composition of claim 1, wherein the (E) oil comprises at least one of (i) a higher fatty acid containing 8 to 20 carbon atoms and (ii) a higher alcohol containing 8 to 20 carbon atoms.

6. The oil-in-water emulsion composition according to claim 5, wherein the (E) oil includes a higher fatty acid, and wherein the higher fatty acid comprises isostearic acid.

7. The oil-in-water emulsion composition according to claim 5, wherein the (E) oil includes a higher alcohol, and wherein the higher alcohol comprises isostearyl alcohol.

8. The oil-in-water emulsion composition of claim 2, wherein the emulsion particles with the internal oil phase each have a diameter of 50 to 1,000 nm.

9. A method for producing an oil-in-water emulsion composition comprising;
　(I) a step of mixing
　　(A) a polyoxyethylene phytosterol,
　　(B) a glycerin fatty acid diester,
　　(C) a polyoxyethylene-polyoxypropylene random copolymer dialkyl ether,
　　(D) an oil-soluble drug, and
　　(E) oil
　to form an oil component mixture containing a layered gel structure having a crystal structure of bimolecular membranes composed of the components (A) and (B);
　(II) a step of adding an aqueous component containing (F) water into the oil component mixture obtained in step (I); and
　(III) a step of mixing to form an oil-in-water emulsion.

10. An oil-in-water emulsion cosmetic product comprising the oil-in-water emulsion composition of claim 1.

11. The oil-in-water emulsion composition of claim 2, wherein the (C) polyoxyethylene-polyoxypropylene dialkyl ether random copolymer comprises a polyoxyethylene-polyoxypropylene dimethyl ether random copolymer.

12. The oil-in-water emulsion composition of claim 2, wherein the (D) oil-soluble drug is one or more selected from the group consisting of an emollient agent, a skin-whitening agent, a skin roughness-preventing agent, an ultraviolet absorber, an anti-inflammatory agent, vitamins, and an antioxidant.

13. The oil-in-water emulsion composition of claim 3, wherein the (D) oil-soluble drug is one or more selected from the group consisting of an emollient agent, a skin-whitening agent, a skin roughness-preventing agent, an ultraviolet absorber, an anti-inflammatory agent, vitamins, and an antioxidant.

14. The oil-in-water emulsion composition of claim 2, wherein the (E) oil comprises at least one of (i) a higher fatty acid containing 8 to 20 carbon atoms and (ii) a higher alcohol containing 8 to 20 carbon atoms.

15. The oil-in-water emulsion composition of claim 3, wherein the (E) oil comprises at least one of (i) a higher fatty acid containing 8 to 20 carbon atoms and (ii) a higher alcohol containing 8 to 20 carbon atoms.

16. The oil-in-water emulsion composition of claim 4, wherein the (E) oil comprises at least one of (i) a higher fatty acid containing 8 to 20 carbon atoms and (ii) a higher alcohol containing 8 to 20 carbon atoms.

17. The oil-in-water emulsion composition of claim 11, wherein the emulsion particles with the internal oil phase each have a diameter of 50 to 1,000 nm.

18. The oil-in-water emulsion composition of claim 14, wherein the emulsion particles with the internal oil phase each have a diameter of 50 to 1,000 nm.

19. An oil-in-water emulsion cosmetic product comprising the oil-in-water emulsion composition of claim 2.

20. An oil-in-water emulsion cosmetic product comprising the oil-in-water emulsion composition of claim 3.

21. The oil-in-water emulsion composition according to claim 1, comprising:
　1-15% by mass of (A) the polyoxyethylene phytosterol;
　1-10% by mass of (B) the glycerin fatty acid diester;
　10-60% by mass of (C) the polyoxyethylene-polyoxypropylene random copolymer dialkyl ether;
　0.0001-10% by mass of (D) the oil-soluble drug;
　5-25% by mass of (E) oil; and
　10-80% by mass of (F) water.

* * * * *